(12) United States Patent
Reaser, Jr.

(10) Patent No.: US 8,774,897 B2
(45) Date of Patent: Jul. 8, 2014

(54) PATIENT-READABLE PORTABLE CARDIAC MONITOR

(71) Applicant: Vernon N. Reaser, Jr., Victoria, TX (US)

(72) Inventor: Vernon N. Reaser, Jr., Victoria, TX (US)

(*) Notice: Subject to any disclaimer, the term of this patent is extended or adjusted under 35 U.S.C. 154(b) by 0 days.

(21) Appl. No.: 13/655,429

(22) Filed: Oct. 18, 2012

(65) Prior Publication Data

US 2014/0114167 A1 Apr. 24, 2014

Related U.S. Application Data

(63) Continuation of application No. 13/385,594, filed on Oct. 18, 2011, now abandoned.

(51) Int. Cl.
*A61B 5/0404* (2006.01)
*A61B 5/0408* (2006.01)
*A61B 5/00* (2006.01)
*A61B 5/046* (2006.01)
*A61B 5/04* (2006.01)

(52) U.S. Cl.
CPC ............... *A61B 5/046* (2013.01); *A61B 5/746* (2013.01); *A61B 5/7455* (2013.01); *A61B 5/04085* (2013.01); *A61B 5/7405* (2013.01); *A61B 5/0404* (2013.01); *A61B 5/04012* (2013.01)
USPC ........................... 600/393; 600/515; 600/518

(58) Field of Classification Search
CPC .. A61B 5/0404; A61B 5/04085; A61B 5/046; A61B 2560/0468

USPC ........................................... 600/393, 515, 518
See application file for complete search history.

(56) References Cited

U.S. PATENT DOCUMENTS

| | | | | | |
|---|---|---|---|---|---|
| 3,830,227 | A | * | 8/1974 | Green | 600/514 |
| 5,172,698 | A | * | 12/1992 | Stanko | 600/510 |
| 7,117,031 | B2 | * | 10/2006 | Lohman et al. | 600/516 |
| 7,197,351 | B2 | * | 3/2007 | Umeda et al. | 600/393 |
| 8,332,019 | B2 | * | 12/2012 | Shimuta et al. | 600/509 |
| 2007/0021676 | A1 | * | 1/2007 | Han et al. | 600/509 |
| 2008/0249426 | A1 | * | 10/2008 | Kuo et al. | 600/523 |
| 2010/0317958 | A1 | * | 12/2010 | Beck et al. | 600/391 |

FOREIGN PATENT DOCUMENTS

| | | | |
|---|---|---|---|
| JP | 1998-234688 A | 9/1998 |
| JP | 1999-299740 A | 11/1999 |
| JP | 2000-279385 A | 10/2000 |
| JP | 2006-110180 A | 4/2006 |

OTHER PUBLICATIONS

International Search Report, Korean Intellectual Property Office, Jan. 28, 2013.

* cited by examiner

*Primary Examiner* — Lee S Cohen
(74) *Attorney, Agent, or Firm* — Seth A. Horwitz; Robert O. Groover

(57) ABSTRACT

Systems and devices to gather data from a subject's heart, analyze said data to determine whether the subject is experiencing cardiac arrhythmia, and display results of said determining. Use, and display of cardiac condition information, are preferably simple and unambiguous to untrained users.

14 Claims, 10 Drawing Sheets

PATIENT-READABLE PORTABLE CARDIAC MONITOR

CROSS-REFERENCE

The present application is a continuation of and claims priority from U.S. patent application Ser. No. 13/385,594, now abandoned, which is hereby incorporated by reference.

BACKGROUND

The present application relates to testing for medical conditions. More particularly, the present application relates to portable detection of cardiac arrhythmia.

Note that the points discussed below may reflect the hindsight gained from the disclosed inventions, and are not necessarily admitted to be prior art.

Atrial fibrillation is the most common form of cardiac arrhythmia, and involves the two upper chambers of the heart. Atrial flutter is a distinct form of cardiac arrhythmia, but has symptoms similar to atrial fibrillation, and similar potential risks (atrial fibrillation and atrial flutter will be collectively referred to herein "AFib"). A trained medical technician or Doctor can usually recognize the unique heart contractions related to AFib. Trained medical personnel can generally detect AFib by taking a patient's pulse, but it takes training and experience that most lay persons lack. Typically, a doctor will use a 12-lead (12 contact) EKG to make a definitive determination of AFib.

Generally, individuals are at high risk to develop AFib beginning at age 65. Ten thousand people per day turn 65 in the U.S. alone. Other people at risk of developing AFib include adolescents, due to the increasing popularity of energy drinks; diabetics; and those who have a close family member who has experienced AFib.

The costs of health care are rising quickly, and rapid access to emergency health services is perennially uncertain.

AFib can be generally be treated successfully if the victim is properly and timely screened. Screening and prompt treatment are far less expensive than treatment of the results of untreated AFib. Left untreated for longer than 48 hours, AFib can lead to a debilitating stroke or death.

A significant proportion of people with untreated AFib will die or be permanently and seriously disabled, likely requiring full time medical care. Millions of people—potentially 30 million in the U.S.—are already at risk, and therefore in need of screening, for AFib. Millions of people may have unknowingly experienced AFib.

Some people can tell when they are in AFib, typically from prior experience, but the vast majority cannot or will not admit to themselves that they have some irregularity in their heartbeat. A large proportion of the population experiences irregular heartbeats from time to time. Most irregular heartbeat incidents are self limiting or benign, but some are not.

There are many excuses for people who suspect they might have AFib to not go to a doctor to be tested. For example, making and keeping an appointment with a doctor (or visiting an emergency room) can be arduous, time consuming and nerve-wracking. First you have to make appointment with a doctor; then take off work to go; drive to the doctor's office and find a parking place nowhere near the office; wait in the waiting room; wait in an exam room; move to another room to take the EKG; and wait in the exam room for the doctor to provide the results. Given such difficulty, AFib sufferers may prefer to ignore their symptoms or treat themselves rather than seek out testing.

Further, a negative EKG in a doctor's office may not be definitive. A person who has an EKG with negative results may have intermittent or paroxysmal AFib, and the episode may have abated when tested. In these instances the most common current solution is to wear a Holter monitor for 24 to 48 hours. Holter monitors are difficult to put on and to keep in place, and are extremely unpleasant to try to sleep in. Another common approach is to use an "event monitor", which is generally worn for up to a month.

Many people suffer infrequent episodes of AFib with long periods of normal rhythm between episodes. These people may be afraid to discontinue their medications, blood thinners and rhythm drugs, because they have no convenient method to easily, and within 48 hours, determine if they are back in AFib. Consequently, they continue taking medication, which is very expensive and carries with it many side effects, some very serious, especially if use is long term.

SUMMARY

Systems and devices for portable detection of cardiac arrhythmia conditions using unambiguous outputs to display cardiac condition information to an untrained user, and methods for using same.

BRIEF DESCRIPTION OF THE DRAWINGS

The disclosed inventions will be described with reference to the accompanying drawings, which show important sample embodiments and which are incorporated in the specification hereof by reference, wherein.

DETAILED DESCRIPTION OF SAMPLE EMBODIMENTS

Figure 1:
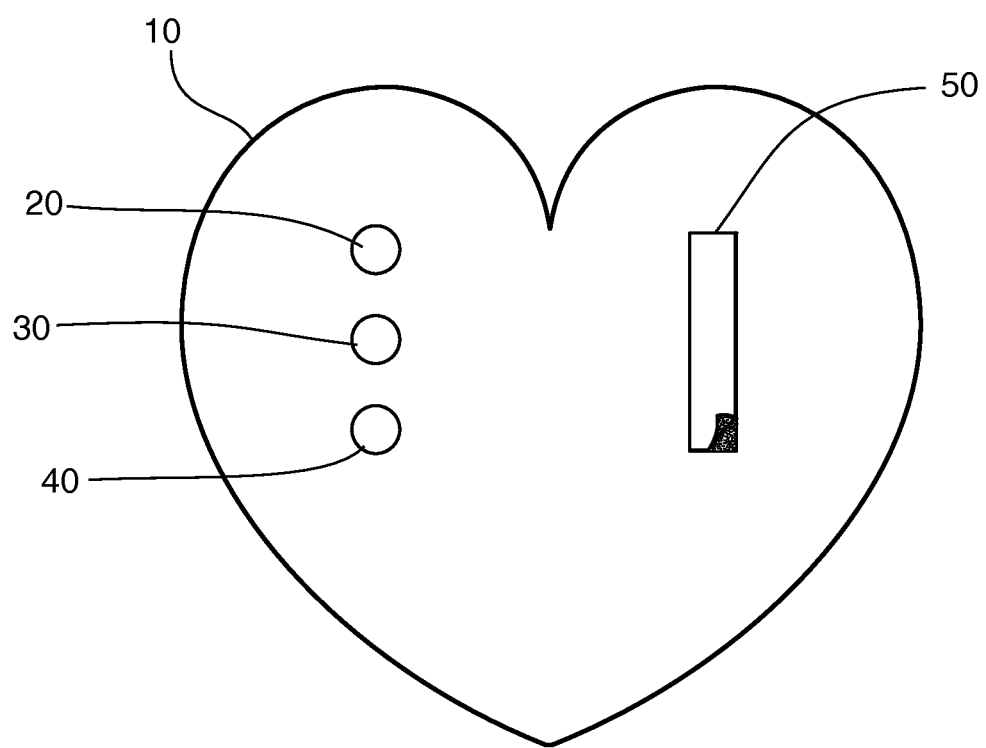
FIG. 1 shows an example of an AFib detector.

The numerous innovative teachings of the present application will be described with particular reference to presently preferred embodiments (by way of example, and not of limitation). The present application describes several inventions, and none of the statements below should be taken as limiting the claims generally.

The present application discloses new approaches to medical screening for cardiac arrhythmia, including systems, devices and methods for portable screening for atrial fibrillation. Inventive embodiments allow easy, inexpensive and rapid determination of whether the subject is experiencing an episode of AFib. Herein, a "subject" is a person on whom an inventive embodiment is used; a "user" is a person, who can have any or no medical training whatsoever, who uses an inventive embodiment on a subject. The user can be the subject or e.g., if the subject is incapacitated, someone who places, activates and reads results of testing displayed by an inventive embodiment. A user can also be, for example, a family member or caretaker who frequently spends time with someone who is at-risk for AFib.

Some embodiments are handheld, and allow deployment, activation and reading using a single hand. Some embodiments can be held and/or used in one hand. Advantageously, embodiments are easy to hold and use; at-risk groups include the elderly, who can have, e.g., arthritic or trembling hands.

Advantageously, a subject can screen him or herself using an inventive embodiment, and given ease and speed of use of such embodiments, can do so on a regular basis without outside diagnostic intervention or requirement of medical or other skill.

Some embodiments are, advantageously, small enough to fit in a clothes pocket, user friendly and easily portable, to provide rapid, self-administered testing without requiring medical professional intervention to determine whether an arrhythmia event has been detected. An unambiguous display shows a user whether or not the screening subject is experiencing an episode of AFib.

Preferred embodiments rapidly provide users and subjects with a direct response regarding whether the subject is currently experiencing atrial fibrillation. This response can be preliminary, in that professional medical diagnostic attention and, if necessary, treatment should immediately be sought if a positive AFib detection is displayed. However, this preliminary flag to seek immediate medical care does not require further diagnostic activity or any medical or other skill; if AFib is detected, the user and/or subject is immediately and clearly informed of that fact.

Some embodiments have a brief series of pictograms giving users or subjects instructions for use of the device. For example, pictograms can show (1) a user subject with her hand over her heart, adjacent to a finger pushing the activation button used in some embodiments; (2) a user subject with her hand over her heart with a red circle mimicking the red LED used in some embodiments to indicate positive detected AFib, adjacent to a red cross; and (3) a user subject with her hand over her heart with a green circle mimicking the green LED used in some embodiments to indicate negative detected AFib, adjacent to a smiling face.

Inventive embodiments provide easy, inexpensive and rapid determination of whether a subject is experiencing an episode of AFib. Advantageously, a subject can screen him or herself, and given ease and speed of use of an inventive device, can do so on a regular basis without outside diagnostic intervention or requirement of medical or other skill.

Using an inventive embodiment, a subject can be tested for AFib. If AFib is detected, a doctor can prescribe a blood thinner such as Lavosat and allow the patient to self-administer (or a family member or caretaker to regularly administer) to maintain a therapeutic range. Preventative measure also include a subject self-testing (or a family member or caretaker testing) for INR to be sure the subject is in normal range.

A doctor can also prescribe drugs to return a subject's heart to normal sinus rhythm. If the drugs are ineffective, the subject can be cardio-converted or ablated, ablation generally being the last measure when all else fails. AFib testing using inventive embodiments can help monitor a subject to make sure a subject does not experience (or continue to experience) AFib.

FIG. 1 shows an example exterior-facing side of a portable AFib detector. Preferably, as shown, a portable detector comprises a pad 10, which can be advantageously formed in the shape of a Valentine heart, and can be made of a flexible material. While such flexible material can, generally, be any material suitable for embedding detector components, such material is preferably particularly conducive to embedding low voltage, low power connections in order to minimize power usage. The Valentine heart shape clearly indicates to users from a broad array of cultures that the device should be placed over the heart for use. For example, for (U.S.A) American users, the ability to place one's hand over one's heart when saying the pledge of allegiance is all the skill required for a subject/user to screen herself.

The front of the pad 10 comprises a red light 20, a yellow light 30 and a green light 40, respectively representing when lit: affirmative AFib detection, at least one error condition, and a negative AFib detection. The front of the pad 10 further comprises a flap 50 for access to a battery 60 (e.g., in a battery compartment 120) used to power the portable detector. The front of the pad 10 can also comprise an activation button 140 (or switch or other activation paradigm) to activate the data-gathering, analysis and display functions and procedures of the portable detector.

Figure 1A:
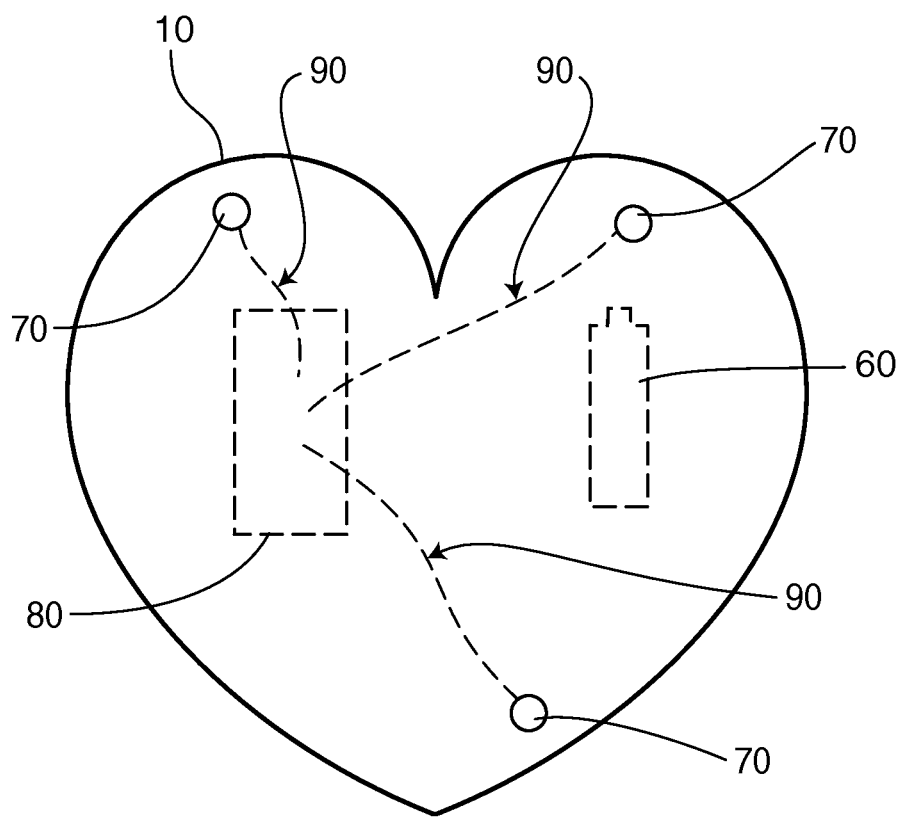
FIG. 1a shows an example of an AFib detector.

FIG. 1a shows an example contact (body-facing, e.g., chest-facing) side of a portable AFib detector. A battery 60, preferably embedded in the pad 10, is used to power the device. Contact points 70 are used for electrocardiogram sensors, comprise conductive material used to gather electrocardiogram data (i.e., cardiac electrical impulses) from a subject's heart, and should be placed on a subject's chest near the heart; the Valentine shape of the pad 10 is intended to aid in proper placement of said contacts 70. Three or more electrocardiogram contact points 70 are generally ample for collection of sufficient and sufficiently accurate data to determine whether a subject is experiencing AFib.

The pad 10 further contains a processing unit 80, preferably embedded in the pad 10, to determine R-R intervals and the presence or lack of discernible P waves in the QRS complex. The processing unit 80 is connected to the contact points 70, by leads 90 (e.g., electrical wires or optical fibres) or wirelessly, to receive the cardiac data collected by said contact points 70. If the processing unit 80 is connected to said contact points 70 by leads 90, it is preferable that said leads 90 be flexible.

Generally, a processor 80 can be programmed to recognize the irregular cardiac patterns that indicate AFib.

Processor 80, 370 programming 360 can include, be fine-tuned in light of, or otherwise be made in at least partial dependence on a subject's medical history.

Indicator outputs, e.g., LED lights 190 or other one-bit visual display outputs, can be used to display AFib detection results to minimize the possibility of user confusion regarding detection results.

The processor 80 and indicator outputs 20, 30, 40 can be integrated into the pad 10, advantageously in the body of the pad 10 or on a skin-opposing side.

An adequately conductive material can be used for the contact points 70 for detection, such as gold, platinum or silver. The leads 90 are attached to the contact points 70 and the processing unit (processor), which sends processed data to the indicator outputs 20, 30, 40. Typically, no ionizing gel is required, though gel or other means of improving conductive skin contact can be used.

Some inventive embodiments can be configured so that a result is displayed to the user within 5 to 10 seconds. Some embodiments can be configured to take a longer period of time to gather additional cardiac data.

In preferred embodiments, output display is as simple as possible. For example, a green light 40 (e.g., an LED) can be used to indicate the absence of AFib, and a red light 20 can be used to indicate the detected presence of AFib.

In some embodiments, a pleasant song or noise can play for the absence of AFib, and an unpleasant song, alarm noise, siren, air raid sound, or other unpleasant or warning sound can play to indicate the detected presence of AFib.

In some embodiments, a pleasant vibration (e.g., gentle) or other movement can be induced to indicate the absence of AFib, and an unpleasant vibration (e.g., violent) or other movement can be induced to indicate the presence of AFib.

In some embodiments, the only displayed output for medical information (as opposed to, e.g., battery status, sufficiency of collected data or correctness of sensor placement) is an indicator for whether AFib has been detected.

In some embodiments, different types of output (visual, sound, touch) are used together.

A preferred embodiment comprises a Valentine heart-shaped flexible pad 10 with an integrated battery compartment 120 for a battery 60 providing power, three electrically conductive contacts 70 on a skin-facing side of the pad 10 to collect cardiac electrical data, flexible wires connecting said contacts 70 to an integrated processing unit 80 analyzing said data, and wires connecting said processing unit 80 to three LED indicators on an exterior-facing side of the pad 10 respectively corresponding to affirmative, negative, and error-status results of AFib detection.

In some embodiments, other indicator outputs are included, such as to inform the user of an error, e.g., improper sensor placement (with respect to the heart or, in some embodiments, a location for pneumatic or acoustic data collection such as certain locations on the neck or an arm), to indicate activation or battery status, or to provide other medical information (e.g., heart rate). Indicator outputs can take the form of any signaling method, such as variously colored lights, variously toned or spaced beeps, various songs, various vibrations or other induced movements, or an LCD or other text or video display.

In some embodiments, output display for detected (or nondetected) AFib is isolated from other output display, so that the risk that a user mistakes or misses displayed information regarding detected (or nondetected) AFib as a result of other displayed information is minimized. Isolation between output displays can be achieved using distance, difference in type of display (e.g., LED versus LCD, text versus video, visual versus sound or music versus beeps), difference in display timing (e.g., immediately versus delayed), or pronounced prominence of AFib information.

Figure 2A:
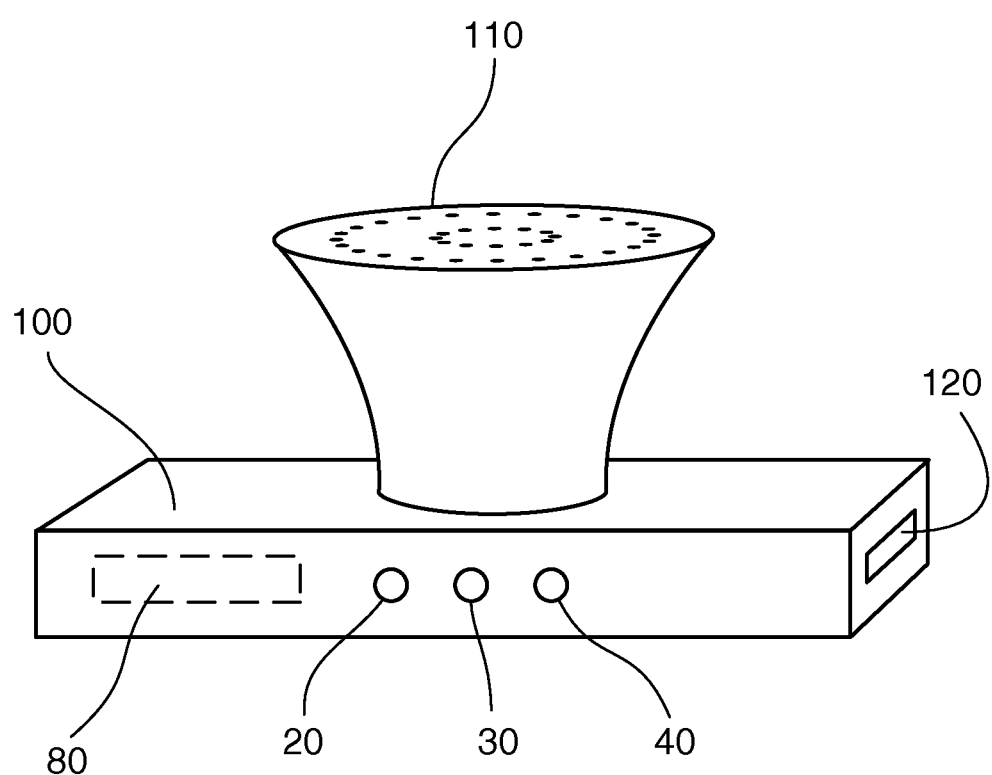
FIG. 2a shows an example of an AFib detector.
Figure 2B:
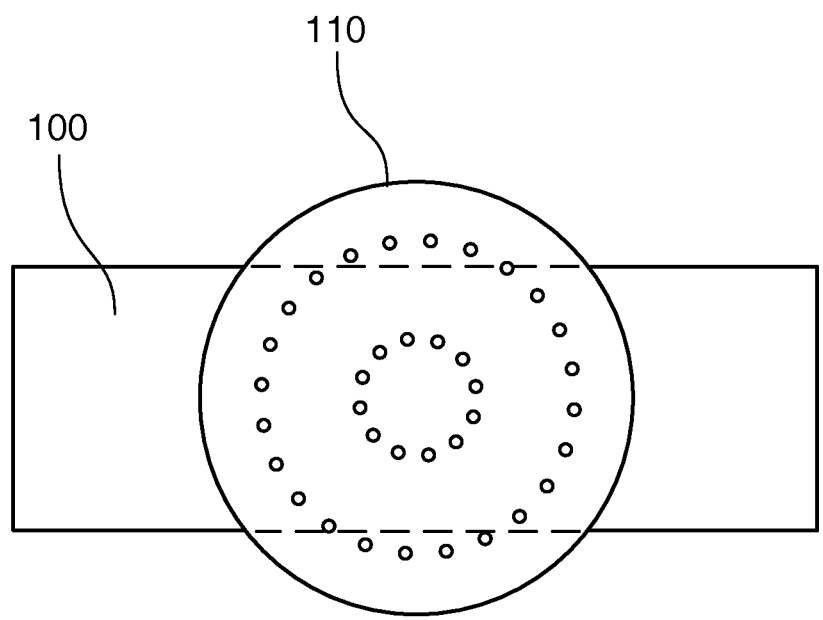
FIG. 2b shows an example of an AFib detector.

FIG. 2a shows an example of an AFib detector. Detector components are preferably integrated into a detector body, e.g., an equipment case 100. One or more acoustic sensors, e.g., a microphone 110, are used to monitor and collect data regarding the contractions of the heart. A microphone 110 can be placed, e.g., over the heart or on either side of the neck close to the windpipe. A red light 20, a yellow light 30 and a green light 40 (e.g., LEDs, OLEDs or other light sources), respectively represent when lit: affirmative AFib detection, at least one error condition, and a negative AFib detection. A battery compartment 120 contains the battery 60, which provides a power source for the detector. A microprocessor 80 (or other processing unit) analyzes data collected by the microphone 110 and displays results using the colored lights. FIG. 2b shows a top view of the portable AFib detector shown in FIG. 2a.

Generally, people know the locations to place an acoustic sensor, and little or no training is required for proper placement.

Once placed in the proper position on a subjects chest—generally, approximately over the heart—an acoustic embodiment can be manually or automatically activated. Manual activation can include, for example, pressing or switching an activation control, or pushing the device onto the subject's chest with sufficient pressure to trigger a pressure sensor, or running a finger across a capacitive sensor. Automatic activation can include, for example, awakening from a sleep mode, such as when a small voltage across electrical contacts 70 allows the device to sense electrical properties commensurate with the contacts 70 touching a subject's skin, or when a capacitive sensor is activated.

Acoustic sensing detects the sounds produced or caused by the contractions of the heart, which are sent to a processor 80 for interpretation.

Typically, detection of adequate data for reliable indication of atrial fibrillation using acoustics takes 15 to 30 seconds, though more or less time can be taken—e.g., prior to commencing AFib information display, or by the user before and/or after commencing AFib information display—depending on, for example, sensor sensitivity, sophistication of analysis software, and a desired level of accuracy.

Figure 3:
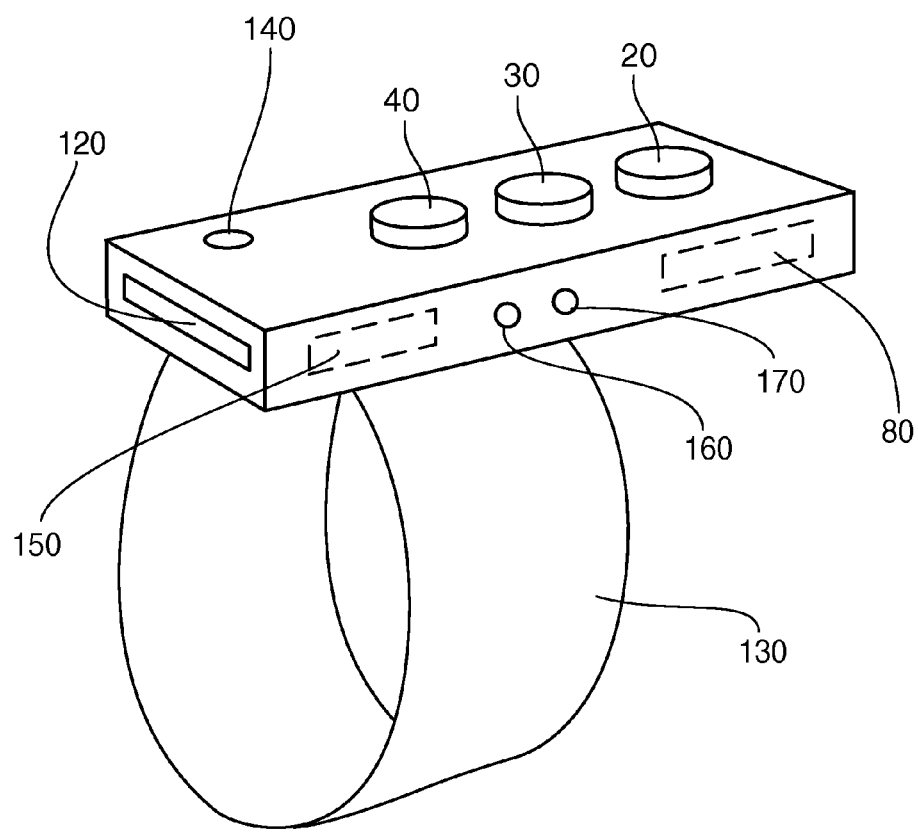
FIG. 3 shows an example of an AFib detector.

FIG. 3 shows an example of a portable AFib detector. When an inflatable cuff 130 is properly fitted on a subject, e.g., on the subject's wrist, and an activation button 140 is depressed, an air pump 150 interior to a housing takes in air through an air intake (through which the air will eventually be released), and inflates an inflatable cuff 130, which comprises a pneumatic sensor. An air intake light 160, separated from AFib detection indicators (e.g., on a different side of the housing), indicates when the cuff 130 is being inflated. Cuff 130 inflation is similar to inflation of a blood pressure test cuff; however, the cuff 130 does not slowly deflate as with a blood pressure test. The cuff 130 remains inflated to a pressure that allows the processor 80 to obtain sufficient data regarding heart contractions of the user, via the user's pulse, to determine whether or not the user is experiencing AFib. Said data is sent to and analyzed by a processing unit 80, e.g., a microprocessor, and the results of AFib detection are displayed. A red light 20, a yellow light 30 and a green light 40 (e.g., LEDs, OLEDs or other light sources), respectively represent when lit: affirmative AFib detection, at least one error condition, and a negative AFib detection. When data collection is complete, a deflate light 170 is activated while the cuff 130 deflates.

A pneumatic sensing portable detector can also be configured for automatic activation, e.g., when contact is sensed with substantially all of the circumference of the inflatable cuff 130.

Generally, sufficient data can be collected using a pneumatic device or method to provide a result to the user within 30 to 60 seconds.

Once the result is displayed the cuff 130 can be deflated and removed by the user.

Figure 4:
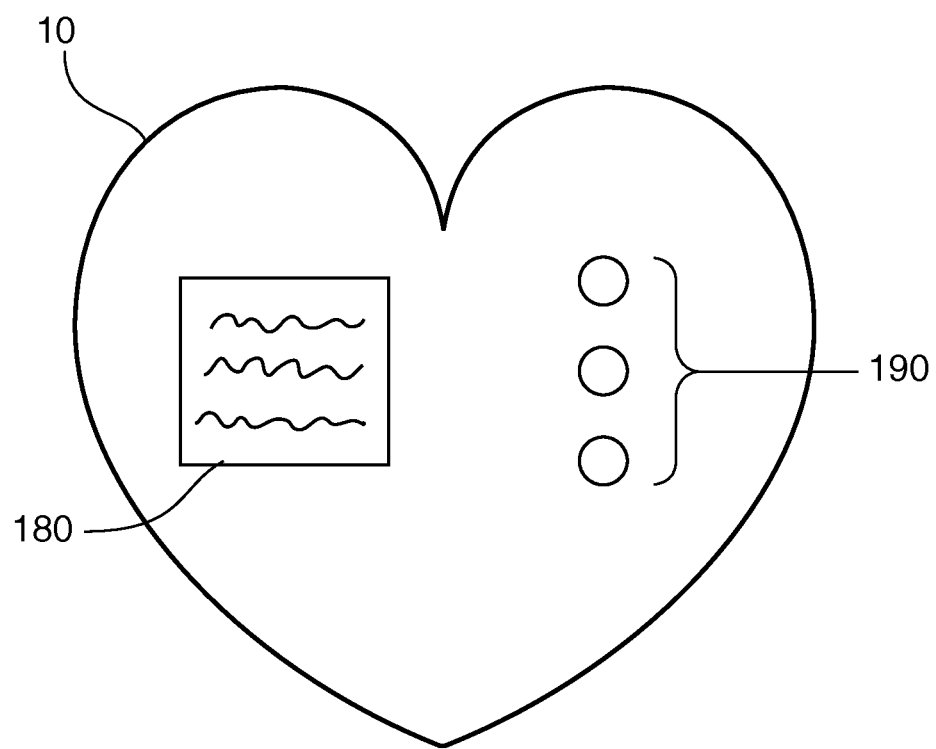
FIG. 4 shows an example of an AFib detector.

FIG. 4 shows an example of an exterior-facing side of an AFib detector. The exterior-facing side has an integrated LCD screen 180 physically separated from integrated LEDs 190. If the LCD screen 180 can display any information typically displayed by an LCD screen, e.g., AFib detection information or other output based on raw or analyzed data collected by integrated cardiac sensors; then preferably, the LEDs 190 display substantially only AFib detection-related information, e.g., positive, negative, and error-related AFib detection results. Conversely, if the LEDs 190 display information other than AFib detection information, then preferably, the LCD screen 180 displays substantially only AFib detection-related information, e.g., positive, negative, and error-related AFib detection results. Some embodiments, as shown here, advantageously attempt to make perception of a display portion comprising AFib results on an inventive AFib detector a distinct act—requiring at least some amount of change in perceptual focus—from perception of other display(s) on said detector (which can be displaying distinct information, but is not necessarily).

Figure 5:
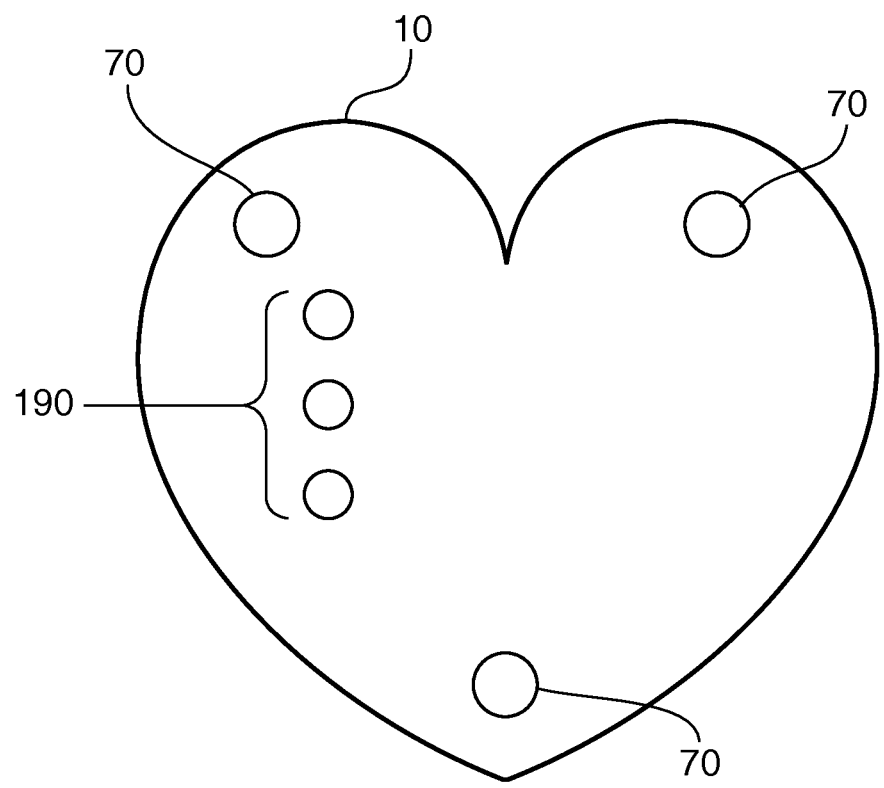
FIG. 5 shows an example of an AFib detector.

FIG. 5 shows one side of an AFib detector with two substantially identical sides. The two surfaces of the pad 10 are substantially functionally and visually identical. Differences between the two sides might include, for example, a flap 50 or panel for battery 60 access, i.e., a difference which would usually not affect activating and reading AFib information from an inventive device. The exterior of the detector has, on both sides, electrical contacts 70 (though, generally, other sensors will also work here) for detection of cardiac data and LEDs to display AFib detection results. LEDs can be recessed into the pad 10 to facilitate a good connection between the contacts 70 and a subject's skin. A processing unit 80, leads 90, and other elements can be embedded inside a pad 10 or approximately flush with a surface. A manual activation button 140 can also be incorporated into each side of the pad 10.

Figure 6:
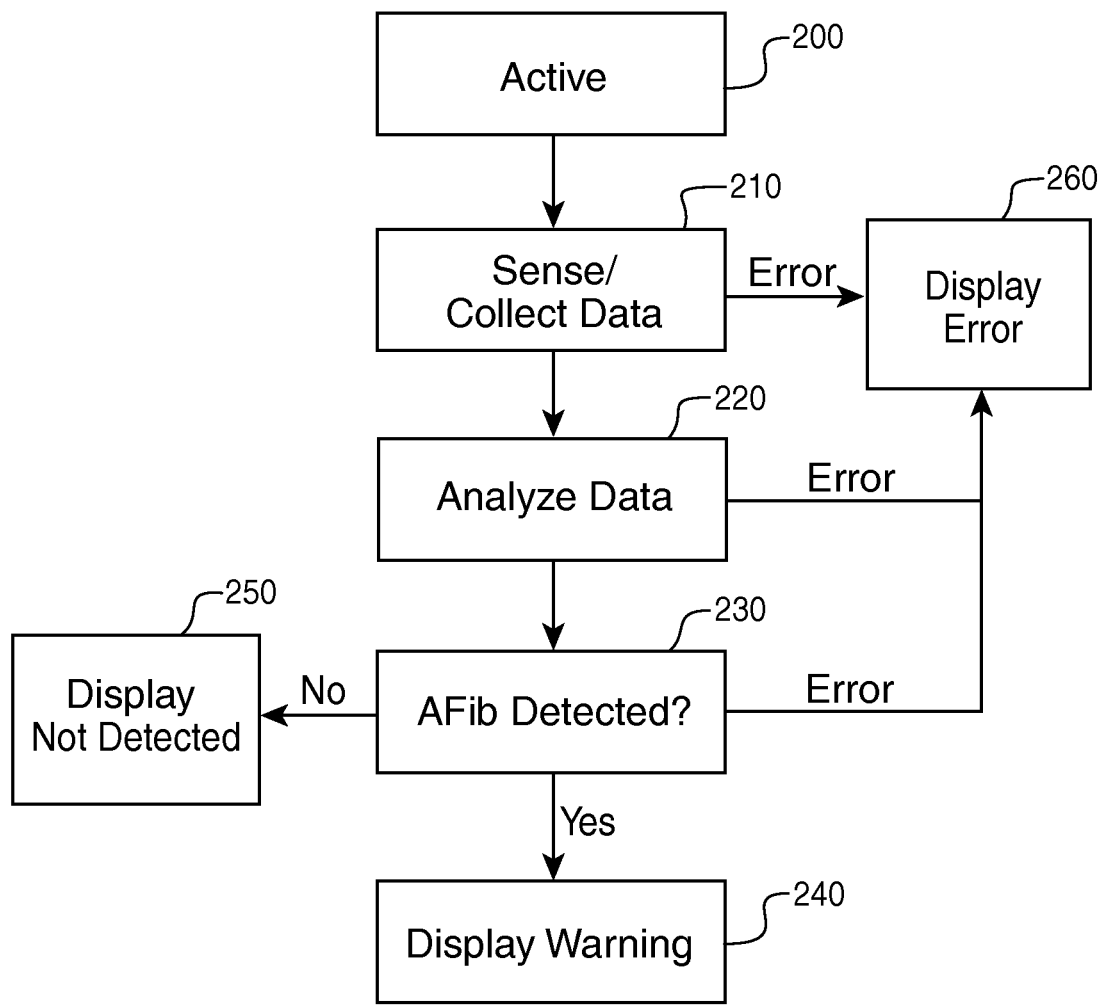
FIG. 6 shows an example of a method of using an AFib detector.

FIG. 6 shows an example of a method of using a portable AFib detector. After an AFib detector is activated 200, the sensor is activated and beings to collect data 210. After sufficient data collection—e.g., after a specified time has passed, or a processing unit 80 has decided that sufficient data has been collected, or a particular data signal has been detected, or analysis has concluded, or an interrupting error condition has occurred (i.e., an error condition that prevents or makes pointless further data collection), data collection stops. Data analysis 220 by a processing unit 80 can begin concurrently with, partially concurrently with or after data collection. Data analysis uses a processing unit 80 to determine at least whether collected data indicate that a subject is experiencing AFib. If AFib is detected 230, then a warning output is displayed 240. If AFib is not detected, then a non-detection output is displayed 250. If an error—e.g., low battery, insufficient data signal strength (such as from a poor connection with the skin or insufficient pneumatic pressure), bad data (such as from a misplaced sensor), inconclusive data, insufficient data, or a malfunction—an error is displayed 260 and the process either terminates or repeats from data collection, depending on the type of error.

Figure 7:
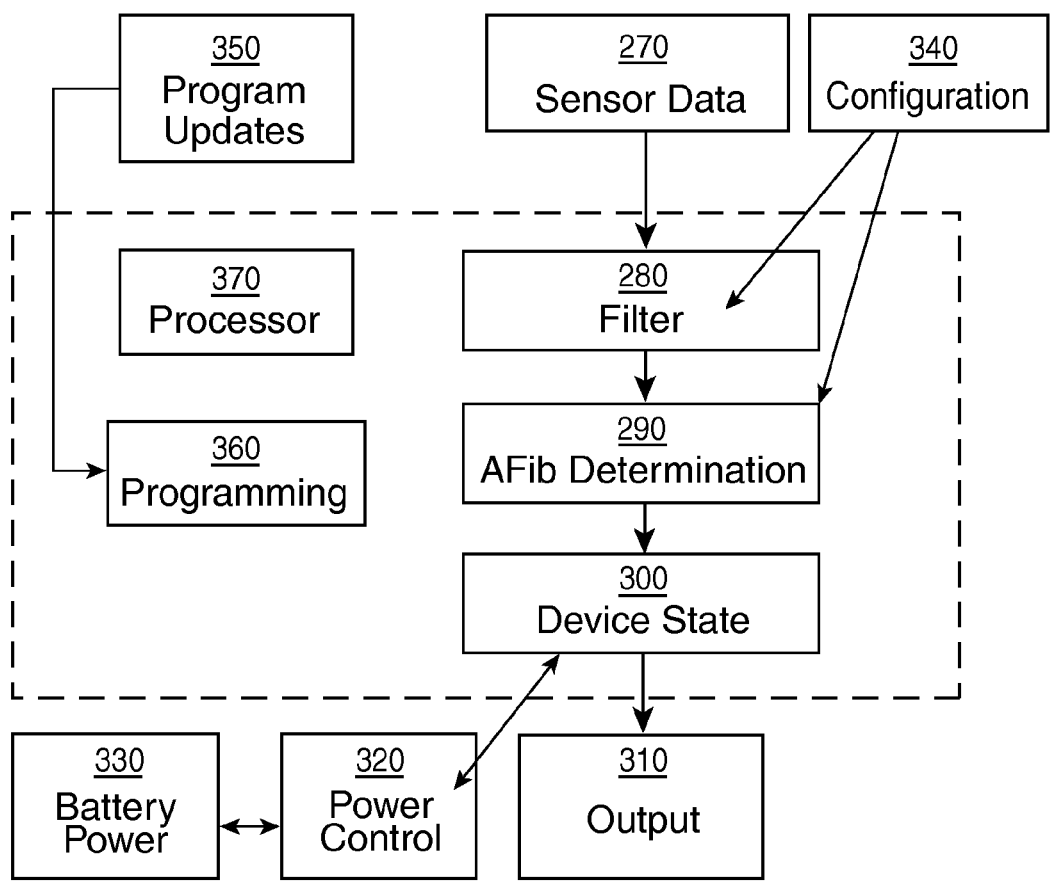
FIG. 7 schematically shows an example of process and data flow in an AFib detector.

FIG. 7 schematically shows an example of process and data flow in an AFib detector. Collected sensor data 270 passes through a filter 280, which passes relevant cardiac data to AFib determination 290, which changes a device state 300, e.g., a memory and/or output flags and/or action signal flags and/or error flags, based on whether it is determined that the subject is experiencing AFib. The device state 300 can be reflected in output 310, e.g., as AFib determination information. The device state 300 can also affect or be affected by power levels as determined and managed at power control 320 (which can include power on/off and power regulation), e.g., if there is insufficient battery power 330 to power the device or if power levels of the device are low an error state can be sent to output 310; or if an error state occurs in data collection (sensor data) or at AFib determination. Error states are also displayed at output 310. Configuration 340 can be used to tune function of the filter 280 or AFib determination 290, which can also affect behavior of device state. Program updates 350, for example using access ports or wifi, can modify programming 360, which affects and, to the extent allowed by hardware, determines global function. Filter 280, AFib determination 290 and device state 300 are functions of a processing unit 370.

Figure 8:
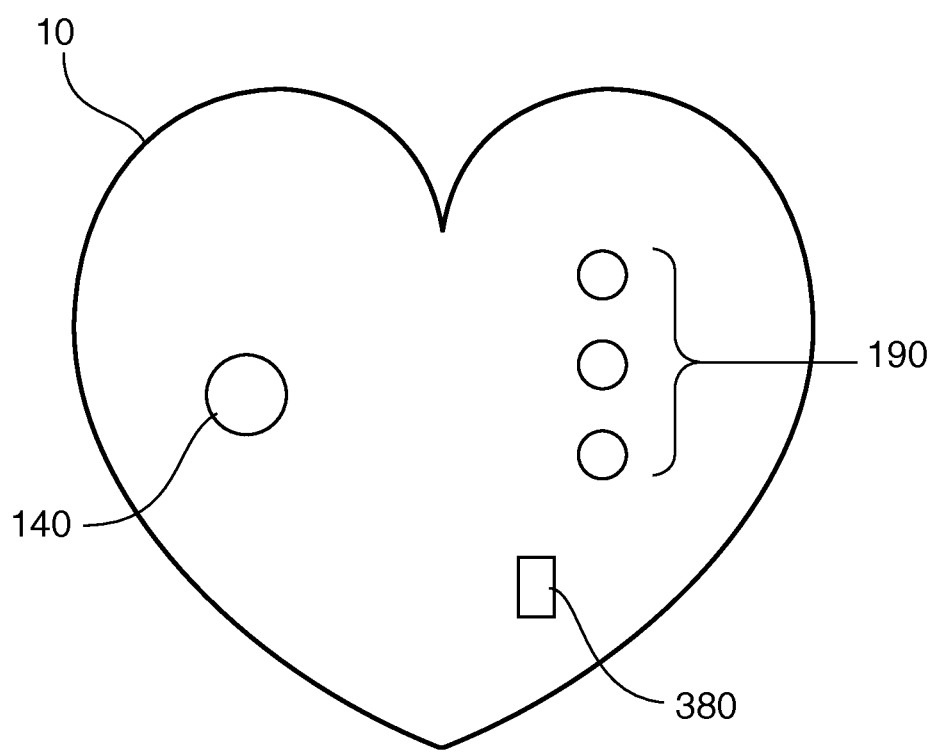
FIG. 8 shows an example of a portable AFib detector.

FIG. 8 shows an example of a portable AFib detector. A portable AFib detector, e.g., those shown in FIGS. 1-5, will have some form of output display, such as output LEDs 190, and can also, as shown, have an activation button 140 (or other form of manual activation toggle) for manual activation of the detector. A communications port 380, which can be wired or wireless, and which may be incorporated into, e.g., the processor 80, can be used to upload or download medical history information or collected sensor data, add program updates 350, modify configuration 340, or otherwise communicate with the AFib detector.

In some embodiments, AFib information is the most prominently displayed output information—e.g., soonest, brightest, loudest, largest, comprising the most types of display (e.g., visual and sound as opposed to only visual, or LED and LCD as opposed to only LCD), comprising the most touch locations or largest touch area on a physical embodiment, and/or comprising the most easily felt vibrations or movements.

In some embodiments, the character of AFib information display is made to immediately be perceived as distinct without requiring a manual for understanding, so that it is difficult to miss displayed AFib information, or to miss displayed AFib information as a result of confusion caused by other displayed information.

In some embodiments, once sensors are properly located on the skin, the user is informed within seconds of his or her status. For example, red, yellow and green low voltage lights can be used as indicator outputs, with red to indicate the user is experiencing AFib, green to indicate the user is not experiencing AFib, steady yellow to indicate improper placement or insufficient data available for processing, blinking yellow to indicate low battery power 330, and lack of any illumination when activated to indicate no battery power 330 or that the device in inoperable.

In some embodiments, the pad 10 contains a sensor to turn the device on and off when placed on or removed from the skin. Such an automatic on/off sensor can enhance ease of use and prolong battery life. Greater energy efficiency can allow use of smaller batteries. Smaller batteries, in turn, can make it easier to use a smaller and lighter electronics housing, which can make it easier for elderly or otherwise infirm users to diligently carry and use an inventive device.

In some embodiments, power efficient output display is used to prolong battery life.

Some embodiments can be configured to be powered by any compatible power source, such as rechargeable batteries or by plugging in to a wall socket.

In some embodiments, the heart shaped pad 10 and its attachments or incorporated components comprise the entirety of an inventive device, and can be formed so that the pad 10 and attachments/components can be rolled up and placed in an easily portable tube, e.g., a tube similar in size and shape to a cigar case.

According to some embodiments, an inventive device does not require post-manufacturing configuration before being used to determine whether a person is experiencing AFib.

In some embodiments, sensor data can be recorded for review on a display of an inventive device or for transmission to another device.

In some embodiments, an inventive device can be configured to allow subject-specific calibration, by a physician or otherwise.

In some embodiments, an inventive device has one or more ports or other means for connecting to the Internet or otherwise to another device, such as a USB or micro-USB (or other type of) port or wireless communications (e.g., wifi) structure and other relevant communications hardware and software. Such connection provides a way to, for example, transmit recorded sensor data to another device or to the cloud; allow remote review of sensor data; or allow remote configuration of the inventive device.

Some embodiments include software or hardware security, e.g., encryption or password protection, for communications using a means for connection such as a USB, micro-USB, or other port.

Some embodiments include user-accessible controls on the device, e.g., an activation control, a power control, or display controls. Preferably, controls are placed and designed to not interfere with AFib information display. Preferably, activation and power controls, if any, are the most prominent controls. Preferably, any controls that could cause confusion are designed to be unobtrusive.

Preferably, embodiments do not require assistance from trained personnel or the help of a lay person.

Some embodiments can be used standing, sitting or in a supine position.

The disclosed innovations, in various embodiments, provide one or more of at least the following advantages. However, not all of these advantages result from every one of the innovations disclosed, and this list of advantages does not limit the various claimed inventions.

- simple displays enable lowered pricing;
- easy to use;
- easily read results;
- easily understood results;
- usable by those with poor eyesight or who are easily confused;
- does not require additional testing and/or analysis to detect AFib and display detection results;
- portable;
- compact;
- lightweight;
- easy to carry and diligently use;
- can be configured to allow targeting to the special needs and medical history of the user; and
- fewer false negatives and positives.

According to some but not necessarily all disclosed innovations, there is provided: a handheld system for detecting atrial fibrillation, comprising: a cordless body having multiple electrodes on at least one surface thereof, which can be pressed against a human chest to make electrical contact; a processing unit, inside said cordless body, which is operatively connected to receive signals from said electrodes, and which is configured to determine from said signals whether atrial fibrillation is occurring; and at least two indicators on said cordless body which are not displays; wherein said processing unit is configured to activate a first one of said indicators when said processing unit determines that atrial fibrillation is NOT occurring, and is configured to active a second one of said indicators when said processing unit determines that atrial fibrillation IS occurring; wherein said body does not show any display or indicators except said two indicators.

According to some but not necessarily all disclosed innovations, there is provided: a handheld system for detecting atrial fibrillation, comprising: a cordless body having multiple electrodes on both faces thereof, so that either face can be pressed against a human chest to make electrical contact; a processing unit, inside said cordless body, which is operatively connected to receive signals from said electrodes, and which is configured to determine from said signals whether atrial fibrillation is occurring; and at least two indicators on each face of said cordless body which are not displays; wherein said processing unit is configured to activate a first one of said indicators when said processing unit determines that atrial fibrillation is NOT occurring, and is configured to active a second one of said indicators when said processing unit determines that atrial fibrillation IS occurring.

According to some but not necessarily all disclosed innovations, there is provided: a handheld system for detecting atrial fibrillation, comprising: a body having multiple electrodes on at least one surface thereof, which can be pressed against a human chest to make electrical contact; a processing unit, inside said cordless body, which is operatively connected to receive signals from said electrodes, and which is configured to determine from said signals whether atrial fibrillation is occurring; and at least two indicators on said cordless body which are not displays; wherein said processing unit is configured to activate a first one of said indicators when said processing unit determines that atrial fibrillation is NOT occurring, and is configured to active a second one of said indicators when said processing unit determines that atrial fibrillation IS occurring; wherein said body does not show any display or indicators except said two indicators.

According to some but not necessarily all disclosed innovations, there is provided: a method for emergency response without medical or emergency response personnel, comprising: pressing electrodes of a detector body against the chest of a person who is suspected of cardiac distress; wherein said detector body has at least two indicator lights on its exterior, but has no display on its exterior; said detector body having a processing unit, in its interior, which is operatively connected to said electrodes and can detect atrial fibrillation, and is configured to activate a first one of said indicator lights when said processing unit determines that atrial fibrillation is NOT occurring, and is configured to active a second one of said indicator lights when said processing unit determines that atrial fibrillation IS occurring; whereby, when said second indicator light is activated, untrained personnel are able to summon emergency personnel, and/or follow predetermined emergency procedures, without waiting for medical interpretation.

According to some but not necessarily all disclosed innovations, there is provided: a method for emergency self-assessment without medical or emergency response personnel, comprising: pressing electrodes of a detector body against one's own chest; wherein said detector body has at least two indicator lights on its exterior, but has no display on its exterior; said detector body having a processing unit, in its interior, which is operatively connected to said electrodes and can detect atrial fibrillation, and is configured to activate a first one of said indicator lights when said processing unit determines that atrial fibrillation is NOT occurring, and is configured to active a second one of said indicator lights when said processing unit determines that atrial fibrillation IS occurring; whereby, when said second indicator light is activated, an untrained person can summon emergency personnel, and/or follow predetermined emergency procedures, without waiting for medical interpretation.

According to some but not necessarily all disclosed innovations, there is provided: a handheld system for testing for atrial fibrillation, comprising: at least one sensor configured to gather data from a subject's heart beat; at least one heart signal analyzer determining, in at least partial dependence on said data, whether said subject is experiencing atrial fibrillation; and at least one output displaying an unambiguous distress signal, unconditionally and apart from other displayed information, if said subject is experiencing atrial fibrillation.

According to some but not necessarily all disclosed innovations, there is provided: a method of testing for atrial fibrillation, comprising: gathering data regarding a subject's heart beat using at least one sensor; determining, in at least partial dependence on said data, whether said subject is experiencing atrial fibrillation; and displaying, unconditionally and independently of other displayed information, whether said subject is experiencing atrial fibrillation.

According to some but not necessarily all disclosed innovations, there is provided: a handheld system for testing for atrial fibrillation, comprising: at least one sensor configured to gather data from a subject's heart beat; at least one heart signal analyzer determining, in at least partial dependence on said data, whether said subject is experiencing atrial fibrillation; and at least one output indicating, in dependence on said determining, whether said subject is experiencing atrial fibrillation, said output being separated from other outputs by at least one of principal media type, physical distance, color, increased size or tone.

According to some but not necessarily all disclosed innovations, there is provided: a method for testing for atrial fibrillation, comprising: gathering data regarding a subject's heart beat using at least one sensor; determining, in at least partial dependence on said data, whether said subject is experiencing atrial fibrillation; and displaying, in dependence on said determining, whether said subject is experiencing atrial fibrillation, said displaying being separated from other displaying by at least one of principal media type, physical distance, color, increased size or tone.

According to some but not necessarily all disclosed innovations, there is provided: a portable system for testing for atrial fibrillation, comprising: at least one sensor configured to gather data from a subject's heart beat; at least one heart signal analyzer determining, in at least partial dependence on said data, whether said subject is experiencing atrial fibrillation; and at least one output indicating, in dependence on said determining, whether said subject is experiencing atrial fibrillation, said output being substantially the only output relating to patient status.

According to some but not necessarily all disclosed innovations, there is provided: a method for testing for atrial fibrillation, comprising: gathering data regarding a subject's heart beat using at least one sensor; determining, in at least partial dependence on said data, whether said subject is experiencing atrial fibrillation; and displaying, in dependence on said determining, whether said subject is experiencing atrial fibrillation, said displaying being substantially the only displaying relating to patient status.

According to some but not necessarily all disclosed innovations, there is provided: a portable system for testing for atrial fibrillation, comprising: at least one sensor configured to gather data from a subject's heart beat; at least one heart signal analyzer determining, in at least partial dependence on said data, whether said subject is experiencing atrial fibrillation; and at least one output indicating, in dependence on said determining, whether said subject is experiencing atrial fibrillation, said output being the only output relating to patient status.

According to some but not necessarily all disclosed innovations, there is provided: a handheld system for testing for atrial fibrillation, comprising: at least one sensor configured to gather data from a subject's heart beat; at least one heart signal analyzer determining, in at least partial dependence on said data, whether said subject is experiencing atrial fibrillation; and at least one output indicating, in at least partial dependence on said determining, whether said subject is experiencing atrial fibrillation, said output comprising a different sensory interface from other outputs.

According to some but not necessarily all disclosed innovations, there is provided: a portable system for testing for atrial fibrillation, comprising: at least one sensor configured to gather data from a subject's heart beat; at least one heart signal analyzer determining, in at least partial dependence on said data, whether said subject is experiencing atrial fibrillation; and a plurality of outputs, separate ones of said outputs being configured to respectively indicate that said subject is or is not currently experiencing atrial fibrillation, said indicating being in at least partial dependence on said determining.

According to some but not necessarily all disclosed innovations, there is provided: a handheld system for testing for atrial fibrillation, comprising: at least one sensor configured to gather data from a subject's heart beat; at least one heart signal analyzer determining, in at least partial dependence on said data, whether said subject is experiencing atrial fibrillation; and at least one output indicating, in at least partial dependence on said determining, whether said subject is experiencing atrial fibrillation, said output not being primarily visually linguistic.

According to some but not necessarily all disclosed innovations, there is provided: a portable system for testing for atrial fibrillation, comprising: at least one sensor configured to gather data from a subject's heart beat; at least one heart signal analyzer determining, in at least partial dependence on said data, whether said subject is experiencing atrial fibrillation; and at least one output indicating, in at least partial dependence on said determining, whether said subject is experiencing atrial fibrillation, wherein said sensor, analyzer and output do not require post-manufacture configuration.

According to some but not necessarily all disclosed innovations, there is provided: systems and devices to gather data from a subject's heart, analyze said data to determine whether the subject is experiencing cardiac arrhythmia, and display results of said determining; use, and display of cardiac condition information, are preferably simple and unambiguous to untrained users.

MODIFICATIONS AND VARIATIONS

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

Embodiments described hereinabove have been described with respect to AFib. However, inventive embodiments can also be configured to perform tests and display results for cardiac conditions other than AFib.

In some embodiments, a display can have one or more aural, visual and/or haptic outputs.

In some embodiments, a rigid or semi-rigid casing, pad (instead of a flexible pad) or other housing or mounting is used to provide structure to components of an AFib detector.

Some embodiments have only outputs that do not comprise text.

In some embodiments, AFib information outputs do not comprise text.

Some embodiments can detect medical, cardiac or cardiac arrhythmia conditions other than AFib.

In some embodiments, colors other than green, yellow and red can be used for output displays comprising lights.

In some embodiments, two electrical contacts 70 can be sufficient to provide accurate results to an electrocardiograph sensor.

In some embodiments, cardiac arrhythmia, or other heart-related irregularities, other than atrial fibrillation and atrial flutter can be detected and processed, and resulting subject status information displayed, e.g., in the unambiguous and/or isolated and/or prominent manner described for AFib.

In some embodiments, a processing unit determines only whether a subject is experiencing AFib.

In some embodiments, the only displayed information is whether a subject is experiencing AFib.

In some embodiments, if a processing unit determines whether a subject is experiencing AFib, then a display unconditionally displays whether the subject is experiencing AFib.

In some embodiments, whether a subject is experiencing AFib is displayed independently, apart from, visually isolated from, perceptually isolated from, or spatially separated from other displayed information.

In some embodiments, a sensor can be separated from a body of a detector and replaced with a different sensor, e.g., a sensor of a different type.

In some embodiments, a detector comprises a plurality of outputs comprising different sensory types, e.g., visual and haptic, a plurality of said output types contemporaneously, concurrently and/or simultaneously displaying a distress signal if AFib is detected.

In some embodiments, display output types used to display positive AFib detection comprise at least two of haptic, visual and audible.

In some embodiments, display output showing positive AFib detection comprises an indication of emergency and/or non-emergency immediately recognizable within a culture of the user or to people having the geographical origin, current residence or preferred language of the user.

In some embodiments, a body of a detector comprises pictorial representations of a method of use of said detector, said pictorial representations being tailored to be immediately comprehensible based on a culture, geographical origin, current residence or preferred language of the user.

In some embodiments, display output for AFib detection results comprises spoken language.

In some embodiments, display output for AFib detection results comprises at least one different sensory or media type from any other medical information display output of the detector.

In some embodiments, display outputs are primarily non-visually-linguistic, i.e., do not comprise written language.

In some embodiments, the only user-accessible controls are power on/off and/or an activation button or other activation one- or two-way (i.e., on only or on/off) toggle.

In some embodiments, controls other than or in addition to power on/off and an activation toggle are implemented, e.g., to control an LCD display.

Additional general background, which helps to show variations and implementations, may be found in the following publications, all of which are hereby incorporated by reference: U.S. patent application Ser. No. 12/613,488; U.S. patent application Ser. No. 11/101,880; U.S. patent application Ser. No. 12/538,467; U.S. patent application Ser. No. 12/811,632; U.S. patent application Ser. No. 12/517,228; U.S. Pat. No. 7,818,049; U.S. patent application Ser. No. 11/610,955; U.S. Pat. No. 7,899,526; U.S. Pat. No. 7,324,850; U.S. patent application Ser. No. 10/239,524; U.S. Pat. No. 6,871,089; U.S. Pat. No. 6,748,260; U.S. Pat. No. 7,266,405; U.S. Pat. No. 7,085,601; U.S. Pat. No. 5,735,285; U.S. Pat. No. 5,682,902; U.S. Pat. No. 5,191,891; U.S. Pat. No. 5,311,449; U.S. Pat. No. 4,340,065; U.S. patent application Ser. No. 12/418,260; U.S. patent application Ser. No. 12/933,425; U.S. Pat. No. 7,630,756; U.S. Pat. No. 7,734,335; U.S. Pat. No. 7,477,936; U.S. Pat. No. 7,147,633; U.S. Pat. No. 6,847,836; U.S. Pat. No. 6,970,737; U.S. Pat. No. 6,389,308; U.S. Pat. No. 6,006,132; U.S. Pat. No. 5,987,352; U.S. Pat. No. 5,876,351; U.S. Pat. No. 5,716,380; U.S. Pat. No. 5,658,316; U.S. Pat. No. 5,544,661; U.S. Pat. No. 5,345,362; U.S. Pat. No. 5,111,396; U.S. Pat. No. 4,974,600; U.S. Pat. No. 4,619,265; U.S. Pat. No. 4,625,730; U.S. Pat. No. 3,814,105; U.S. patent application Ser. No. 12/359,223; U.S. patent application Ser. No. 11/449,591; U.S. patent application Ser. No. 11/383,235; U.S. patent application Ser. No. 11/319,640; and http://www.newcardio.com/products-cardio-bip.php and all other material within the www.newcardio.com website.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A handheld system for detecting atrial fibrillation, comprising:
    a Valentine heart-shaped cordless body having multiple electrodes on both faces thereof, so that either face can be pressed against a human chest to make electrical contact;
    a processing unit, inside said cordless body, which is operatively connected to receive signals from said electrodes, and which is configured to determine from said signals whether atrial fibrillation is occurring; and
    at least two indicators on each face of said cordless body which are not displays;
    wherein said processing unit is configured to activate a first one of said indicators when said processing unit determines that atrial fibrillation is NOT occurring, and is configured to active a second one of said indicators when said processing unit determines that atrial fibrillation IS occurring, and
    wherein said Valentine heart shape of said body provides a culture-specific indication of an operationally-correct position and orientation for placement of said body, on a subject's chest and over the subject's heart with said Valentine heart shape facing upward, and
    whereby front/back orientation is made irrelevant to placing said body in said operationally-correct position.

2. The system of claim 1, wherein said body does not show any display or indicators except said two indicators.

3. The system of claim 1, wherein each face of said body has a third indicator thereon which is not a display.

4. The system of claim 1, wherein each face of said body has a third indicator thereon which is not a display, and each face of said body does not show any display or indicators except said three indicators.

5. The system of claim 1, wherein said body also contains a power source.

6. The system of claim 1, wherein said body does not include any display nor external electrical connection.

7. The system of claim 1, wherein said body also contains an audible alarm, and said processor is configured and operatively connected to also sound said alarm when atrial fibrillation is occurring.

8. The system of claim 1, wherein said body also contains a vibration mechanism, and said processor is configured and operatively connected to also activate said vibration mechanism when atrial fibrillation is occurring.

9. The system of claim 1, wherein said body also contains an audible alarm and a vibration mechanism, and said processor is configured and operatively connected to also sound said alarm and activate said vibration mechanism when atrial fibrillation is occurring.

10. The system of claim 1, wherein each face of said body carries only three of said electrodes.

11. A handheld system for detecting atrial fibrillation, comprising:
- a cordless body having multiple electrodes on both faces thereof, so that either face can be pressed against a human chest to make electrical contact;
- a sensor on each face of said cordless body, said sensors configured to automatically determine when said body has been placed against a subject's chest;
- a processing unit, inside said cordless body, which is operatively connected to receive signals from said electrodes, and which is configured to determine from said signals whether atrial fibrillation is occurring once said sensors determine that said body has been placed against the subject's chest; and
- at least two indicators on each face of said cordless body which are not displays;
- wherein said processing unit is configured to activate a first one of said indicators when said processing unit determines that atrial fibrillation is NOT occurring, and is configured to active a second one of said indicators when said processing unit determines that atrial fibrillation IS occurring,
- whereby front/back orientation is made irrelevant to placing said body in an operationally-correct and automatically-activating position on the subject's chest.

12. The system of claim 11, wherein at least one face of said body does not show any display or indicators except said two indicators.

13. The system of claim 11, wherein each face of said body has a third indicator thereon which is not a display.

14. The system of claim 11, wherein each face of said body has a third indicator thereon which is not a display, and each face of said body does not show any display or indicators except said three indicators.

\* \* \* \* \*